(12) United States Patent
Kishita et al.

(10) Patent No.: US 6,703,003 B1
(45) Date of Patent: Mar. 9, 2004

(54) MANICURE COMPOSITION FOR NAIL

(75) Inventors: Kazutaka Kishita, Rancho Palos Verdes, CA (US); Nobuo Ohsawa, Torrance, CA (US)

(73) Assignees: Three Bond Co., Ltd., Tokyo (JP); Three Bond International Inc., West Chester, OH (US)

( * ) Notice: Subject to any disclaimer, the term of this patent is extended or adjusted under 35 U.S.C. 154(b) by 0 days.

(21) Appl. No.: 09/456,485

(22) Filed: Dec. 7, 1999

Related U.S. Application Data

(60) Provisional application No. 60/112,285, filed on Dec. 15, 1998.

(51) Int. Cl.[7] .............................. A61K 6/00; A61K 7/00; A61K 7/04
(52) U.S. Cl. .......................................... 424/61; 424/401
(58) Field of Search ................................ 424/195.1, 61, 424/401

(56) References Cited

U.S. PATENT DOCUMENTS

| 3,507,822 | A | * | 4/1970 | Miyami | 260/31.8 |
|---|---|---|---|---|---|
| 4,384,058 | A | * | 5/1983 | Galante | 524/32 |
| 4,444,933 | A | * | 4/1984 | Columbus et al. | 524/292 |
| 4,626,428 | A | * | 12/1986 | Weisberg et al. | 424/61 |
| 4,726,942 | A | * | 2/1988 | Lang et al. | 424/47 |
| 4,810,498 | A | * | 3/1989 | DiMeglio | 424/195.1 |
| 5,643,581 | A | * | 7/1997 | Mougin et al. | 424/401 |
| 5,824,180 | A | | 10/1998 | Mikuni et al. | 156/275.3 |
| 6,203,802 | B1 | * | 3/2001 | Handjani et al. | 424/401 |

FOREIGN PATENT DOCUMENTS

| JP | 2-91012 | * | 3/1990 | |
| JP | 10-508326 | | 8/1998 | C09J/4/04 |

* cited by examiner

Primary Examiner—Thurman K. Page
Assistant Examiner—S. Howard
(74) Attorney, Agent, or Firm—Sughrue Mion, PLLC

(57) ABSTRACT

A manicure composition for nail, which contains: a cyanoacrylate composition; and a natural oil extracted from a plant, the proportion of the natural oil being from 0.01 to 10 parts by weight per 100 parts by weight of the cyanoacrylate composition.

4 Claims, No Drawings

MANICURE COMPOSITION FOR NAIL

CROSS REFERENCE TO RELATED APPLICATION

This application is an application filed under 35 U.S.C. §111 (a) claiming benefit pursuant to 35 U.S.C. §119(e)(1) of the filing date of the U.S. Provisional Application 60/112,285, filed Dec. 15, 1998, pursuant to 35 U.S.C. §111 (b).

FIELD OF THE INVENTION

This invention relates to a manicure composition for nails, which contains a cyanoacrylate as the main component and exerts a therapeutic effect on chapped nails.

BACKGROUND OF THE INVENTION

It has been a practice to use cyanoacrylate compositions as manicure compositions in treating chapped nails such as those having rough and coarse surface or those in a state where the tip ends thereof are readily cracked. For example, JP-A-58-103406 (the term "JP-A" as used herein means an "unexamined published Japanese patent application".) discloses use of cyanoacrylates as adhesives for adhering artificial nails while JP-A-2-91012 discloses use of cyanoacrylates as enamel coating compositions for nails.

Cyanoacrylates have high hardening rates to the extent that they are generally employed in instantaneous adhesives. However, cyanoacrylates are hardened so quickly that the hardening reaction thereof is associated with heat generation. Therefore, when cyanoacrylates are applied to nails, there arises heat irritation.

To relieve the heat irritation with respect to skin, JP-W-A-10-508326 (the term "JP-W-A" as used herein means an "published Japanese national stage of international application".) discloses a technique of adding dioctyl phthalate serving as a plasticizer to cyanoacrylates.

Nails, which protect fingertips, are composed of overlapping flat epithelial cells made of keratinous protein which contains cystine as the main constituent. Because of being a part of the skin, nails in a healthy, elastic and glossy state contain moisture and lipids which are continuously supplied from the body. Nail chapping proceeds as follows. When the moisture and lipids are eliminated from nails or their supply becomes insufficient, the nails become harder and keratinize. As a result, the epithelial cells are coming loose and falling and thus the nails become rough, less elastic and coarse followed by the occurrence of cracking.

When nails are manicured, it is generally observed that the moisture evaporation/supply in the nails becomes out of balance or lipids are eluted out from the nails. As a result, nail chapping proceeds under the manicure coating. Therefore, the nail chapping can be prevented by adding to manicure compositions a substance capable of keeping nails in good health or improving the nail health. Moreover, it is necessary that such additives never deteriorate the quick hardening properties or storage stability of cyanoacrylates.

SUMMARY OF THE INVENTION

An object of the present invention is to provide a manicure composition which contains a cyanoacrylate as the main component and exerts a therapeutic effect on chapped nails.

Other objects and effects of the present invention will become available from the following description.

The above-described objects of the present invention have been achieved by providing the following manicure composition.

A manicure composition for nail, which contains:
a cyanoacrylate composition; and
a natural oil extracted from a plant, the proportion of the natural oil being from 0.01 to 10 parts by weight per 100 parts by weight of the cyanoacrylate composition.

DETAILED DESCRIPTION OF THE INVENTION

Cyanoacrylates are generally represented by the following structural formula:

$$CH_2=C(CN)-COOR \qquad (1)$$

wherein R represents an alkyl group having from 1 to 5 carbon atoms.

The cyanoacrylate composition for use in the present invention is not particularly limited and can be selected from those commonly employed as instantaneous adhesives. For example, those described in JP-W-A-10-508326, JP-A-58-103406, JP-A-2-91012, etc. can be used.

The natural oil extracted from a plant for use in the present invention includes liquid or solid fats such as olive oil, camellia oil, jojoba oil, avocado oil, mango oil, carnauba wax and rice wax. These natural oils contain, as the main component, ester compounds of higher alcohols having 10 or more carbon atoms, particularly from 10 to 50 carbon atoms, with glycerol. These natural oils may be either unrefined virgin oils or refined ones. Although virgin oils have an advantage of containing additional medicinally efficacious components such as vitamin C and vitamin E, there is a fear that the storage stability of cyanoacrylates might be deteriorated thereby.

Particularly preferred examples of the natural oil include avocado oil and jojoba oil. This is because these oils can suppress the heat generation upon hardening without deteriorating the quick hardening properties of cyanoacrylates or impairing the storage stability thereof. Furthermore, these natural oils are high in the effect of preventing nails from keratinization.

The natural oil content in the manicure composition of the present invention is preferably from 0.01 to 10 parts by weight per 100 parts by weight of the cyanoacrylate composition. This is because natural oil contents of 0.01 part by weight or less do not provide effects of inhibiting the heat generation upon hardening and of preventing nail keratinization sufficiently, and natural oil contents exceeding 10 parts by weight deteriorate the adhesion properties of the cyanoacrylate to provide manicure compositions having inferior coating properties.

The manicure composition of the present invention can be prepared by mixing the above-described cyanoacrylate composition with the above-described natural oil by stirring at room temperature.

Since the nail polish composition of the present invention maintains the inherent quick hardening properties of the cyanoacrylates, a coating made of the composition can be dried quickly. Moreover, since the heat generation upon hardening is suppressed, it relieves heat irritation upon application of the composition. In addition, the lipids contained in the natural oil prevent the nails from keratinization and thus contribute to the maintenance of healthy and elastic nails.

The present invention will be illustrated in greater detail with reference to the following Examples, but the invention should not be construed as being limited thereto.

EXAMPLES 1 to 4 AND COMPARATIVE EXAMPLES 1 AND 2

Formulations of the compositions used as Examples 1 to 4 and Comparative Examples 1 and 2 are shown in Table 1.

In addition, evaluation results of these compositions are shown in Table 2.

TABLE 1

| Component | Ex. 1 | Ex. 2 | Ex. 3 | Ex. 4 | Comp. Ex. 1 | Comp. Ex. 2 |
|---|---|---|---|---|---|---|
| Cyanoacrylate-type adhesive (Three Bond 1742 ™) | 100 | 100 | 100 | 100 | 100 | 100 |
| Avocado oil | 0.01 | 10 | | | 20 | |
| Magnolia oil | | | 3 | | | |
| Carnauba wax | | | | 0.5 | | |
| Olive oil | | | | 0.5 | | |
| Dioctyl phthalate | | | | | | 5 |

TABLE 2

| Evaluation Item | Ex. 1 | Ex. 2 | Ex. 3 | Ex. 4 | Comp. Ex. 1 | Comp. Ex. 2 |
|---|---|---|---|---|---|---|
| Drying/hardening time (sec) | 10 | 20 | 15 | 10 | 60 | 15 |
| Storage stability at 40° C. (days) | >30 | >30 | >30 | >30 | 20 | >30 |
| Gloss/smoothness of coating | good | good | good | good | good | good |
| Strength/adhesion of coating | good | good | good | good | peeling | good |
| Heat irritation | none | none | none | none | none | none |
| Nail state inspection after 30 days | decrease in elasticity | nothing peculiar | nothing peculiar | nothing peculiar | nothing peculiar | keratinization |

The item "gloss/smoothness of coating" was evaluated by observing each dried coating on a nail with the naked eye. The item "strength/adhesion of coating" was evaluated by scratching each dried coating with the tip end of a nail and examining as to whether the coating peeled off or not. The item "heat irritation" was evaluated based on the unpleasantness caused by the heat irritation in the course of the application of each product on a nail followed by drying and hardening. The item "nail state inspection" was evaluated by, 30 days after the application, removing each coating by dissolving in acetone and comparing the conditions of the thus treated nail with an untreated nail.

EXAMPLES 5 TO 23

Manicure compositions were prepared by changing the natural oil used in Example 1 with various natural oils shown in Tables 3 and 4.

The thus prepared manicure compositions were subjected to various evaluations in the same manner as in Example 1. The evaluation results are shown in Tables 5 and 6.

TABLE 3

| Component | Ex. 5 | Ex. 6 | Ex. 7 | Ex. 8 | Ex. 9 | Ex. 10 | Ex. 11 | Ex. 12 | Ex. 13 | Ex. 14 | Ex. 15 | Ex. 16 |
|---|---|---|---|---|---|---|---|---|---|---|---|---|
| Cyanoacrylate-type adhesive (Three Bond 1742 ™) | 100 | 100 | 100 | 100 | 100 | 100 | 100 | 100 | 100 | 100 | 100 | 100 |
| Apricot kernel oil | 0.1 | | | | | | | | | | | |
| Borage oil | | 0.1 | | | | | | | | | | |
| Canola oil | | | 0.1 | | | | | | | | | |
| Evening primrose oil | | | | 0.1 | | | | | | | | |
| Grape seed oil | | | | | 0.1 | | | | | | | |
| Hemp seed oil | | | | | | 0.1 | | | | | | |
| Jojoba oil | | | | | | | 0.1 | | | | | |
| Kiwi fruit seed oil | | | | | | | | 0.1 | | | | |
| Kukui nut oil | | | | | | | | | 0.1 | | | |
| Macadamia nut oil | | | | | | | | | | 0.1 | | |
| Pistachio nut oil | | | | | | | | | | | 0.1 | |
| Rose hip oil | | | | | | | | | | | | 0.1 |

TABLE 4

| | Ex. 17 | Ex. 18 | Ex. 19 | Ex. 20 | Ex. 21 | Ex. 22 | Ex. 23 |
|---|---|---|---|---|---|---|---|
| Cyanoacrylate-type adhesive (Three Bond 1742 ™) | 100 | 100 | 100 | 100 | 100 | 100 | 100 |
| Safflower oil | 0.1 | | | | | | |
| Sesame seed oil | | 0.1 | | | | | |
| Sunflower oil | | | 0.1 | | | | |
| Sweet almond oil | | | | 0.1 | | | |
| Tea tree oil | | | | | 0.1 | | |
| Walnut oil | | | | | | 0.1 | |
| Wheat germ oil | | | | | | | 0.1 |

TABLE 5

| Evaluation Item | Ex. 5 | Ex. 6 | Ex. 7 | Ex. 8 | Ex. 9 | Ex. 10 | Ex. 11 | Ex. 12 | Ex. 13 | Ex. 14 | Ex. 15 | Ex. 16 |
|---|---|---|---|---|---|---|---|---|---|---|---|---|
| Drying/hardening time (sec) | 15 | 13 | 20 | 25 | 13 | 15 | 10 | 15 | 15 | 20 | 20 | 15 |
| Storage stability at 40° C. (days) | >30 | >30 | >30 | >30 | >30 | >30 | >30 | >30 | >30 | >30 | >30 | >30 |
| Gloss/smoothness of coating | good | good | good | good | good | good | good | good | good | good | good | good |
| Strength/adhesion of coating | good | good | good | good | good | good | good | good | good | good | good | good |
| Heat irritation | none | none | none | none | none | none | none | none | none | none | none | none |
| Nail state inspection after 30 days | nothing peculiar | nothing peculiar | nothing peculiar | nothing peculiar | nothing peculiar | nothing peculiar | nothing peculiar | nothing peculiar | nothing peculiar | nothing peculiar | nothing peculiar | nothing peculiar |

TABLE 6

| Evaluation Item | Ex. 17 | Ex. 18 | Ex. 19 | Ex. 20 | Ex. 21 | Ex. 22 | Ex. 23 |
|---|---|---|---|---|---|---|---|
| Drying/hardening time (sec) | 15 | 15 | 15 | 15 | 15 | 15 | 15 |
| Storage stability at 40° C. (days) | >30 | >30 | >30 | >30 | >30 | >30 | >30 |
| Gloss/smoothness of coating | good | good | good | good | good | good | good |
| Strength/adhesion of coating | good | good | good | good | good | good | good |
| Heat irritation | none | none | none | none | none | none | none |
| Nail state inspection after 30 days | nothing peculiar | nothing peculiar | nothing peculiar | nothing peculiar | nothing peculiar | nothing peculiar | nothing peculiar |

The manicure composition of the present invention supplies lipid components to nails and thus prevents the nails form keratinization. Therefore, use of the nail polish composition of the present invention makes it possible to maintain elastic and healthy nails.

While the invention has been described in detail and with reference to specific examples thereof, it will be apparent to one skilled in the art that various changes and modifications can be made therein without departing from the spirit and scope thereof.

What is claimed is:

1. A nail polish composition, which comprises:

a cyanoacrylate composition as a major component; and a natural oil extracted from a plant as a minor component, the proportion of the natural oil being from 0.01 to 10 parts by weight per 100 parts by weight of the cyanoacrylate composition.

2. The nail polish composition according to claim 1, wherein said natural oil comprises at least one liquid or solid fat selected from the group consisting of camellia oil, mango oil, rice wax, avocado oil, magnolia oil, carnauba wax, olive oil, apricot kernel oil, borage oil, canola oil, evening primrose oil, grape seed oil, hemp seed oil, jojoba oil, kiwi fruit oil, kukui nut oil, macadamia nut oil, pistachio nut oil, rose hip oil, safflower oil, sesame seed oil, sunflower oil, sweet almond oil, tea tree oil, walnut oil and wheat germ oil.

3. The nail polish composition according to claim 2, wherein said natural oil comprises two or more kinds of solid fats.

4. The nail polish composition according to claim 2, wherein said natural oil comprises avocado oil or jojoba oil.

* * * * *